United States Patent [19]

Spinner

[11] Patent Number: 4,463,205

[45] Date of Patent: Jul. 31, 1984

[54] ALKYLATION PROCESS WITH IMPROVED LINEAR ALKYLBENZENE RECOVERY

[75] Inventor: Joel B. Spinner, Chicago, Ill.

[73] Assignee: UOP Inc., Des Plaines, Ill.

[21] Appl. No.: 529,055

[22] Filed: Sep. 2, 1983

[51] Int. Cl.³ .................................................. C07C 2/66
[52] U.S. Cl. .................................... 585/455; 585/456; 585/464
[58] Field of Search ..................... 585/455, 456, 464

[56] References Cited

U.S. PATENT DOCUMENTS

| | | | |
|---|---|---|---|
| 2,477,382 | 7/1949 | Lewis | 585/19 |
| 3,275,702 | 9/1966 | Hutson, Jr. | 585/456 |
| 3,413,217 | 11/1968 | Kunesh | 585/455 |
| 3,484,498 | 12/1969 | Berg | 585/315 |
| 3,494,971 | 2/1970 | Fenske | 585/449 |
| 3,499,826 | 3/1970 | Sulzbach et al. | 585/455 |
| 3,950,448 | 4/1976 | Witt | 585/449 |
| 4,079,093 | 3/1978 | Winter | 585/456 |
| 4,237,327 | 12/1980 | Winter | 585/456 |
| 4,237,328 | 12/1980 | Winter | 585/456 |

Primary Examiner—Curtis R. Davis
Attorney, Agent, or Firm—James R. Hoatson, Jr.; John F. Spears, Jr.; William H. Page, II

[57] ABSTRACT

A process is disclosed for the production of alkylaromatic hydrocarbons by the alkylation of an aromatic hydrocarbon, such as benzene, with a $C_8$-plus acyclic olefin which preferably is a normal olefin. The hydrocarbonaceous effluent of the alkylation reaction zone is separated by fractional distillation to yield both a product stream containing monoalkylated aromatics and a small bottoms stream containing dialkylated aromatics and other high boiling compounds but which is substantially devoid of the product monoalkylated aromatics. The product stream is a portion of a sidecut stream withdrawn from the first of two vacuum columns, with a second portion of the sidecut being passed into the second column. The bottoms stream of the first column is also passed into the second column and the overhead vapor of the second column enters an upper portion of the first column.

11 Claims, 1 Drawing Figure

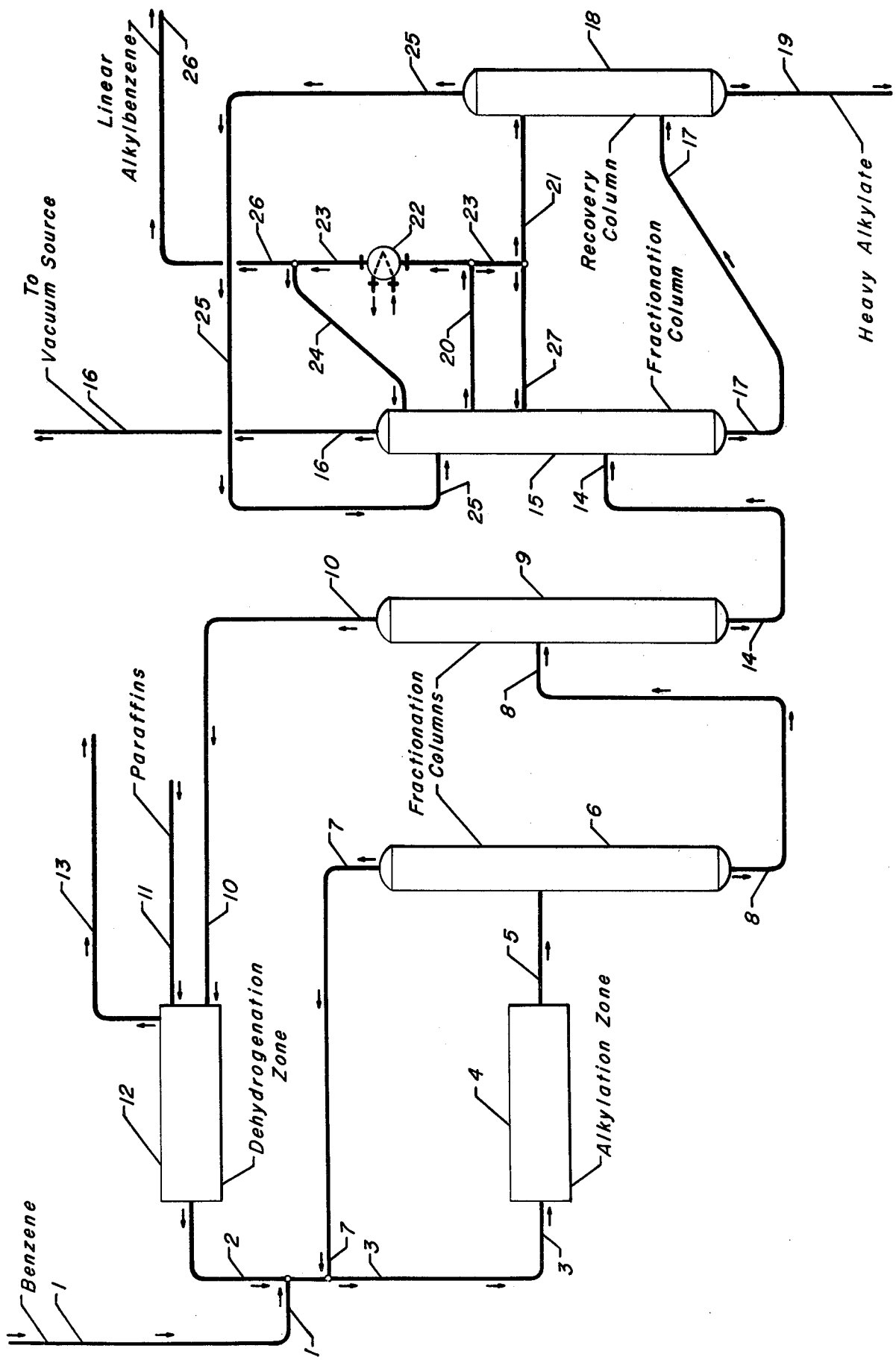

ALKYLATION PROCESS WITH IMPROVED LINEAR ALKYLBENZENE RECOVERY

FIELD OF THE INVENTION

The invention relates to a hydrocarbon conversion process. The invention directly relates to processes for the production of alkylated aromatic hydrocarbons by the reaction of an alkylatable aromatic hydrocarbon with an olefinic hydrocarbon. An example of this is the HF-catalyzed alkylation of benzene with a normal olefinic hydrocarbon, which creates a linear alkylbenzene highly suitable for the production of detergents. The invention specifically relates to the fractional distillation methods employed within such a process to recover the product alkylbenzene from the mixture of lower and higher boiling hydrocarbons with which it exits the alkylation reaction zone.

PRIOR ART

The alkylation of benzene with acyclic olefins is a widely practiced commercial process. This process is performed to produce a variety of chemical compounds which may be end products or may be used as intermediates in the production of other valuable industrial chemicals. One of the most significant processes for the alkylation of aromatic hydrocarbons employs liquid phase HF as the catalyst and is performed to produce alkylbenzenes which are then converted into detergents by sulfonation and neutralization. This process is described in some detail in U.S. Pat. No. 2,477,382 issued to A. H. Lewis and U.S. Pat. No. 3,275,702 issued to T. Hutson, Jr. These references illustrate the fractionation of the alkylation reaction zone effluent in three fractionation columns. The first two columns remove residual benzene and all other hydrocarbons having boiling points below the desired initial boiling point of the product alkylate. The last column splits the remaining hydrocarbons into a net overhead stream containing the product monoalkylbenzenes and a net bottoms product containing heavier hydrocarbons such as dialkylbenzenes.

In a slight variation of this fractionation method, the product fractionation zone comprises four columns, with the first column being an HF stripping column which removes essentially all HF and a small amount of benzene from the hydrocarbon phase leaving the alkylation reaction system. This stripping column could also be considered as part of the alkylation zone. Yet another variation in fractionation zone design is shown in U.S. Pat. No. 3,950,448 issued to P. A. Witt. In this process, the stripping column and the benzene column are combined, with the benzene being removed as a sidecut stream of the first of three columns. The last two columns are operated at a subatmospheric pressure as is customary in the fractionation of high boiling materials such as alkylbenzenes. Both the paraffin stream and the detergent alkylate stream are removed as sidecuts from the last two columns.

The preferred arrangement of the alkylation zone is shown in U.S. Pat. No. 3,494,971 issued to E. R. Fenske. The preferred method of integrating the operation of alkylation zone with a normal paraffin dehydrogenation zone is shown in U.S. Pat. No. 3,484,498 issued to R. C. Berg.

BRIEF SUMMARY OF THE INVENTION

The invention is an improved process for the production of alkylated aromatic hydrocarbons characterized by the unique fractional distillation method which is employed to recover the product hydrocarbons. This fractionation method reduces the amount of the product monoalkylated aromatic which is lost as part of the heavy (high boiling) by-product stream removed from the fractionation zone. The increased recovery is achieved by a facile method of further fractionating the bottoms stream of the column producing the product alkylate without resorting to excessive fractionation temperatures.

A broad embodiment of the invention may be characterized as a process for the production of alkylaromatic hydrocarbons which comprises the steps of contacting a first feed stream comprising a $C_7$-plus olefinic hydrocarbon with a second feed stream comprising an alkylatable aromatic hydrocarbon and with an alkylation catalyst in an alkylation zone operated at alkylation-promoting conditions and thereby producing an alkylation zone effluent stream which comprises a mixture of monoalkylated aromatic hydrocarbons, dialkylated aromatic hydrocarbons and high boiling point alkylation reaction by-products; and recovering a product stream of high purity monoalkylated aromatic hydrocarbon by fractionating the alkylation zone effluent stream in a fractionation zone in which (i) a first process stream which comprises the monoalkylated aromatic hydrocarbon, dialkylated aromatic hydrocarbons, and other high boiling point reaction by-products is passed into a first intermediate point of a first fractionation column operated at a subatmospheric pressure; (ii) a first net bottoms stream comprising the high boiling reaction by-products, dialkylated aromatic hydrocarbons, and monoalkylated aromatic hydrocarbon is removed from the first fractionation column and passed into a second fractionation column operated at a subatmospheric pressure; (iii) a sidecut stream comprising the monoalkylated aromatic hydrocarbon is withdrawn from the first fractionation column at a higher second intermediate point; (iv) the sidecut stream is divided into at least a first portion which is withdrawn as the product stream of the process and a second portion which is passed into the second fractionation column at a point above the location at which the first net bottoms stream enters the second fractionation column third portion; (v) an overhead vapor stream comprising the monoalkylated aromatic hydrocarbon is removed from the second fractionation column and passed into the first fractionation column at a point above said first intermediate point; and (vi) a second net bottoms stream comprising the dialkylated aromatic hydrocarbon is withdrawn from the second fractionation column and removed from the process.

DESCRIPTION OF THE DRAWING

The drawing is a simplified flow diagram of an integrated process for producing linear alkylbenzenes from paraffins and benzene. This representation of a preferred embodiment of the subject process is not intended to exclude from the scope of the subject invention those other embodiments set out herein or the reasonable and normal modifications of those embodiments. Referring now to the drawing, a stream of high purity benzene enters the process through line 1 and is admixed with a recycle benzene stream from line 7 and a stream comprising a mixture of normal paraffins and normal olefins carried by line 2. The resultant hydrocarbon admixture is passed into an alkylation zone 4 through line 3. In the alkylation zone, the reactants are contacted with an alkylation catalyst at alkylation-promoting conditions to thereby affect the production of the product alkylbenzene. There is thereby produced a hydrocarbonaceous alkylation zone effluent stream carried by line 5 which comprises unreacted benzene, the relatively inert paraffinic hydrocarbons, the product alkylbenzene and a mixture of various high boiling reaction by-products.

The alkylation zone effluent stream is passed into a first fractionation column 6 often referred to as the benzene column as it produces a net overhead stream which is rich in benzene and is recycled through line 7. The net bottoms stream of the benzene column is passed through line 8 into a second fractionation column 9 often referred to as the paraffin column. The hydrocarbons entering the paraffin column are separated into an upper product, which may be removed as a sidecut stream, carried by line 10 rich in the paraffins which exited the alkylation zone. These paraffins are transferred through line 10 into a dehydrogenation zone 12 wherein, in admixture with feed $C_{10}$ to $C_{15}$ paraffins from line 11, they are contacted with a dehydrogenation catalyst at dehydrogenation-promoting conditions to affect the conversion of a significant amount of the paraffins to the corresponding olefinic hydrocarbon. The unconverted paraffins and the product olefins are not separated but are transferred to the alkylation zone via line 2. Hydrogen and any light ends produced as by-products of the dehydrogenation reaction are removed through line 13.

The remainder of the hydrocarbons which enter the paraffin column 9 are removed as a net bottoms stream carried by line 14 which comprises a mixture of the desired product monoalkylbenzene and the high boiling by-products. This admixture is passed into a third fractionation column 15. This column is maintained at a subatmospheric pressure through the removal of vapors to a vacuum source through line 16. This column is operated at fractionation conditions which affect the separation of the entering hydrocarbons into the vapor stream of line 16, a sidecut stream removed through line 20 and a net bottoms stream removed through line 17 which is rich in the heavy or high boiling by-products such as the dialkylated benzene. A first portion of the sidecut stream is removed from the process through lines 23 and 26 as the net product stream of the process. The sidecut stream which was withdrawn through line 20 is also divided into a second portion which is passed into an upper portion of the recovery column 18 through line 21 and a third portion which is passed into the third fractionation column via line 24 after being cooled in the indirect heat exchange means 22. A fourth portion of the sidecut stream is preferably returned to the third fractionation column just below the level of its withdrawal via line 27. Essentially all of the monoalkylbenzene which enters the recovery column 18 is removed as part of the overhead vapor carried by line 25 into an upper intermediate point of the column 15. There is thereby produced a heavy alkylate stream removed through line 19 as the net bottoms stream of the recovery column which has a much lower concentration of the product monoalkylbenzene than the heavy alkylate streams of the prior art.

DETAILED DESCRIPTION

One of the more important commercially performed alkylation reactions is the production of detergent grade alkylated aromatic hydrocarbons. This material, often referred to as "detergent alkylate", is normally formed by the reaction of benzene with an olefinic hydrocarbon having from seven to twenty carbon atoms per molecule. A better quality detergent precursor normally results from the use of olefinic hydrocarbons having from about ten to fifteen carbon atoms per molecule. The detergents produced from the resulting alkylated aromatic hydrocarbons are classified either as "soft" if they meet certain standards of biodegradability or as "hard" if they are relatively nonbiodegradable. Soft detergents result from using a long-chain monoolefin as the olefinic reactant. The preferred method of producing these olefins is by the dehydrogenation of the corresponding nonmal paraffins. The dehydrogenation zone may be integrated with the detergent alkylation process as described in U.S. Pat. Nos. 3,413,373; 3,484,498 and 3,494,971. Hard detergents result from the use of branched chain olefins such as propylene tetramer produced in a catalytic condensation process. The use of soft detergents is becoming more widespread, and the subject invention will therefore be discussed primarily in terms of soft detergent production. Also, HF is widely used as the alkylation catalyst, and is the preferred catalyst. The bulk of this description therefore presupposes the use of HF as the catalyst. The invention is however basically a process flow or separation technique which is not specific to the use of any one catalyst. Solid catalysts containing other halogens and/or synthetic materials such as zeolites could be employed as the catalyst.

In the contemporary detergent alkylation process, the product alkylate leaves the alkylation zone in admixture with a number of hydrocarbons including high boiling point reaction by-products. The undesired high boiling by-products include the result of the oligomerization of two or three of the feed acyclic olefins, the dialkylation of the feed aromatic hydrocarbon and the reaction of two or more of the feed aromatic hydrocarbons with a single molecule of the feed olefin. A large number of by-products are therefore possible. These by-products normally lower the quality of the detergent. It is therefore necessary to separate the product monoalkylaromatic from these other hydrocarbons. Heretofore, this separation was performed by fractional distillation as in the manner set out above. The detergent alkylate product is more volatile than the undesired high boiling reaction by-products. In the prior art methods, the detergent alkylate is therefore taken off a fractionation column as a sidecut or an overhead product and the by-products are removed as a net bottoms stream. However, neither the desired detergent alkylate nor the heavy by-products are very volatile. In addition, the detergent alkylate is susceptible to thermal degradation. Subatmospheric pressure fractionation conditions must be employed to achieve a suitable separation without significant thermal degradation. Nevertheless, the total recovery of the product detergent alkylate is not achieved in a typical commercial process unit and the bottoms stream which removes the heavy by-products contains a small but significant amount of the product detergent alkylate. To recover this product material in the prior art fractionation systems would require such extremely low pressures and/or higher reboiler temperatures that an improved separation is not deemed commercially feasible. It is an objective of the subject invention to increase the recovery of monoalkylbenzene in an alkylation process which also produces higher boiling by-products including dialkylbenzene.

The aromatic hydrocarbon which is alkylated in the subject process is preferably benzene, but may be a higher molecular weight aromatic hydrocarbon. The feed aromatic hydrocarbon may therefore be toluene, a xylene, ethylbenzene, phenol, naphthalene, etc. The feed olefinic hydrocarbon which is consumed in the production of the detergent alkylate may have from about seven to twenty carbon atoms per molecule. The olefinic hydrocarbon may be propylene tetramer or a similar material. The preferred olefinic hydrocarbons are aliphatic monoolefins having from ten to fifteen carbon atoms per molecule. When these olefinic hydrocarbons are produced in a dehydrogenation process which is integrated with the alkylation process, it is a common practice to pass the unseparated paraffin-olefin mixture produced as the effluent of dehydrogenation process into the alkylation process as the olefin-containing feed stream. This is basically because of the high cost of separating olefins and paraffins of the same carbon number, but the presence of the paraffins is also beneficial. The normal paraffins act as a heat sink for the heat of reaction and promote monoalkylation by decreasing the overall olefin concentration. The olefin-containing feed stream charged to the alkylation process may therefore contain from about 0 to about 90 mole percent of straight chain paraffins having the same number of carbon atoms per molecule as the olefinic hydrocarbons. These relatively non-reactive paraffins pass through the alkylation process in the various hydrocarbon phase streams and are eventually separated from the alkylate by fractionation and then recycled to the dehydrogenation process.

Chemical reactions which involve olefinic hydrocarbons and are catalyzed by hydrogen fluoride usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid-phase hydrogen fluoride. The desired result is a uniform dispersion and intimate contacting of the hydrocarbon and hydrogen fluoride phases and the avoidance of localized high temperatures or localized high concentrations of either the olefinic hydrocarbon or the hydrogen fluoride. The initial contacting of the reactants and the catalyst has been done in a number of different ways. For instance, the olefinic hydrocarbons have been sprayed into a mixture of hydrogen fluoride and hydrocarbons through nozzles, and mixtures of the reactants have been released into eductors as high velocity streams which cause the eduction and admixture of the hydrogen fluoride. U.S. Pat. No. 4,134,734 describes a unitary reactor for the production of detergent alkylate. U.S. Pat. No. 4,072,730 describes a process for producing detergent alkylate in which a centrifugal pump is utilized as the first reaction zone due to the intense agitation which occurs within the pump.

The alkylation zone preferably has an overall arrangement similar to that shown in previously referred to U.S. Pat. No. 3,494,971. In this arrangement, the two feed hydrocarbons and liquid phase HF are charged to a reactor. The effluent of this reactor is passed into a first settling zone and separated into HF and hydrocarbon phases. The HF is withdrawn and divided into a portion passed into a regenerator and a portion returned to the reactor. A hydrocarbon phase is withdrawn from the first settling zone and charged to a contactor, which is sometimes referred to as a second "reactor" as the only hydrocarbon charged to the contactor. The HF charged to the contactor is a mixture of newly regenerated HF and HF withdrawn from a second settling zone, which receives the total effluent of the contactor. A portion of the HF withdrawn from the second settling zone is charged to the reactor to replace the HF withdrawn for regeneration. The hydrocarbon phase which is withdrawn from the second settling zone may be withdrawn as the alkylation zone effluent stream but is preferably passed into a stripping column in which dissolved HF is removed overhead and some of the feed aromatic hydrocarbon is also recovered. The net bottoms of this HF stripping column becomes the alkylation zone effluent stream charged to the fractionation zone of the subject process.

The alkylation reaction zone is maintained at alkylation-promoting conditions. As used herein, the term "alkylation-promoting conditions" is intended to include a pressure sufficient to maintain the reactants and HF in a liquid phase. A general range of operating pressures is from about 2 to 41 atmospheres absolute. The temperature range covered by this set of conditions is from about −20° to about 95° C., but the reaction is preferably conducted at a temperature of from 15° to 70° C. The volumetric ratio of HF to the total amount of hydrocarbons entering the reactor should be maintained within the broad range of from about 0.2:1 to about 10:1. A preferred range for this ratio is from 0.5:1 to 2:1. To lessen the production of polyalkylated benzenes and to reduce the amount of olefin polymerization in the reactor, the mole ratio of benzene to the monoolefin at the point of initial olefin-acid contact is maintained above 1:1, but preferably below 14:1. A range of typical commercial ratios is from 3:1 to about 10:1.

The conditions maintained within the contactor are similar to the conditions maintained in the reaction zone, but some adjustment is required. For instance, since essentially all of the olefin is preferably consumed in the reactor, the hydrocarbon stream fed to the contactor is substantially free of olefins. There is therefore no benzene to olefin ratio to be specified. The same pressure range may be used in the contactor as in the reactor, but a higher temperature is preferred. This higher temperature should be at least 6 to 10 Centigrade degrees above that used in the reactor. All temperatures specified herein are intended to refer to the average temperature of the liquid stream entering the respective zone.

The acid/catalyst ratio maintained in the contactor will normally be slightly lower, and a typical ratio is about 1:1. The purity of acid used in the contactor will, however, be higher. This is preferred because of the greater effectiveness of higher purity acid for the treatment of the alkylate. This treatment consists of the defluorination of the alkylate product and the extraction of naphthalenes and anthracenes. A higher acid purity is obtained by admixing the newly regenerated acid into the alkylate-containing hydrocarbon stream entering the contactor. The recycle acid for use in the reactor is withdrawn from the second settling zone and therefore contains a higher concentration of high molecular weight hydrocarbonaceous impurities. The acid used in the reactor preferably contains about 85-92 wt. % HF and will typically be about 90 wt. % HF. The acid used in the contactor preferably contains more than 90 wt. % HF and is typically about 93-94 wt. % HF.

The effluent streams leaving the reactor and the contactor will typically be an intimate admixture of liquid phase hydrocarbons and liquid phase hydrogen fluoride. They may be in the form of a true emulsion. A considerable residence time is normally required to separate these two liquid phases, and the effluent streams are therefore passed into settling zones. The two settling zones will normally be maintained at a temperature which is set by the entering HF-hydrocarbon mixtures withdrawn from the respective upstream zones. They will therefore be at substantially the same temperature as the immediately upstream reactor or contactor. The same is also normally true for the pressures used in the settling zones after adjustment for any pressure change due to liquid flow and elevation differences. The settling zones may however be downstream of control valves and therefore operated at a somewhat reduced pressure. This reduced pressure, however, must be superatmospheric and sufficient to maintain liquid phase conditions. A residence time for both the acid and hydrocarbon phases in the settling zones should be in excess of 30 seconds but less than 30 minutes.

Those skilled in the art are familiar with the regeneration of the HF acid-catalysts. Information about the apparatus and conditions utilized for this operation is contained in the previously cited patents and also in U.S. Pat. Nos. 3,721,720 and 3,975,164. The regeneration operation is normally accomplished by stripping the acid under conditions sufficient to decompose alkylfluorides and to produce an overhead vapor stream containing HF and the stripping media. Benzene available within the process is a suitable stripping media. The overhead vapor stream of the column is passed into a condenser, the resultant condensate is allowed to separate into an acid phase and a benzene phase containing dissolved HF. The acid phase is withdrawn as the regenerated HF stream fed to the contactor. The bottoms liquid temperature required in the HF regeneration column will be above about 400° F.

The overhead vapor stream of the HF regeneration column will contain vapor-phase HF and the benzene or other aromatic hydrocarbon which is being alkylated. This vapor stream has a low concentration of the higher boiling impurities which it is desired to remove from the liquid phase HF stream fed to the HF regeneration column. The higher boiling materials are concentrated into a relatively small stream removed from the HF regeneration column as a net bottoms stream. The aromatic hydrocarbon present in the overhead vapor stream of the HF regeneration column is derived mainly from the reflux liquid fed to the top of this column. A small amount of the aromatic hydrocarbon is also dissolved in the liquid phase HF stream fed to HF regeneration column. The reflux liquid is preferably removed from the overhead receiver which collects the condensed overhead of the HF stripping column. It is not necessary to supply reflux liquid for successful operation of the HF regeneration column if the feed stream is passed into the top of the column.

As previously stated, the hydrocarbonaceous phase removed from the second settling zone is preferably passed into a stripping column referred to as the HF stripping column. The function of this column is to prevent the passage of HF into the downstream fractionation zone. Representative conditions for the operation of the HF stripping column include an overhead vapor temperature of about 250° F. at a pressure of approximately 36 psig. There is normally no external reflux to this column. The overhead vapor stream of the HF stripping column is normally condensed by cooling it to about 100° F. or less.

The hydrocarbonaceous effluent of the alkylation zone is passed into a fractionation zone in which the product detergent alkylate is recovered. This fractionation zone is preferably formed by four separate fractionation columns arranged and operated in the manner shown in the drawing. However, numerous variations in the initial separations are possible. For instance, the initial column could separate both the feed aromatic hydrocarbon and the normal paraffins from the remaining hydrocarbons as an upper product, with these two hydrocarbons then being split apart in a different column. The fractionation zone should in some manner produce a process stream which contains the product monoalkylaromatic and the higher boiling by-products. In the subject invention, this process stream is then further separated in two interconnected vacuum columns. Both of these columns preferably employ internal reboilers and have external reflux systems. The process stream enters an intermediate point of the first column. The term "intermediate point" is used herein to indicate a point along the height of a column which is separated from both extremities by at least two real fractionation trays or an amount of packing equal to these two trays. The use of packing is preferred as it results in a lower pressure drop as vapor rises through the column. This first column is designed and operated to separate substantially all of the entering hydrocarbons into a net bottoms stream which contains only a small amount of the product monoalkylaromatic and a sidecut stream which is essentially free of the high boiling alkylation by-products. The sidecut stream is withdrawn at an upper intermediate point preferably separated from the feed point by a band of packing.

The net bottoms of the first column is charged to a lower portion of the second column. A portion of the sidecut from the first column is passed into the upper portion of the second column as an external reflux, with a band of packing being present between the points at which these streams enter the second column. This column is designed and operated to separate the entering hydrocarbons into a small second net bottoms stream having a low concentration of the product monoalkylaromatic hydrocarbon and an overhead vapor stream essentially free of the high boiling by-products. Preferably, this second net bottoms stream contains less than 5 mole percent monoalkylated aromatics. The overhead vapor stream of the second column is passed into an intermediate point of the first column, such as just below the point of the sidecut removal. The sidecut removed from the first column is preferably divided into at least three and preferably four portions. A first portion of this liquid is withdrawn as the product stream of the process; a second portion is fed to the second column. A third portion is fed to the top of the first column as condensing reflux and a fourth portion is fed to an intermediate point of the first column as an external reflux.

Based on the design specifications of a representative commercial scale detergent alkylation process, the process stream charged to the first vacuum column will have a temperature of about 413° F. (212° C.) and have a flow rate of about 69 moles per hour (mph). The vapor emerging from the top of the uppermost packing in this column should be at a pressure of about 10–15 mm Hg absolute with a temperature of approximately 170° F. (76° C.). The uppermost packing acts as a contact condenser. The portion of the sidecut liquid removed from the first vacuum column as the product has a flow rate of about 66 mph. The portion of the sidecut liquid flowing into the second vacuum column has a flow rate of about 19 mph. A cooled portion of sidecut liquid having a flow rate of about 128 mph is injected into the first column above the top packing. The temperature of the liquid being reboiled (flowing to reboiler) in the first column is about 455° F. (235° C.). A first net bottoms stream having a flow rate of about 6 mph is transferred from the first column to the second column. A second net bottoms stream having a flow rate of about 3 mph is withdrawn from the second column. The overhead vapor of the second column has a flow rate of about 22 mph at a temperature of approximately 419° F. (215° C.) and a pressure of about 20 mm Hg absolute. This example is believed highly representative of the preferred embodiment of the invention.

The invention may accordingly be characterized as a process for the production of alkylaromatic hydrocarbons which comprises the steps of contacting a first feed stream which comprises both a $C_8$-plus normal olefinic hydrocarbon and a corresponding paraffinic hydrocarbon with a second feed stream which comprises benzene and with liquid phase HF in an alkylation zone operated at alkylation-promoting conditions and producing a hydrocarbonaceous alkylation zone effluent stream which comprises the paraffinic hydrocarbon, benzene, monoalkylated benzene and dialkylated benzene; separating benzene from the alkylation zone effluent stream in a first fractionation means, and thereby producing a first process stream, which comprises the paraffinic hydrocarbon, monoalkylated benzene and dialkylated benzene; separating paraffinic hydrocarbons from the first process stream in a second fractionation means, and thereby producing a second process stream, which comprises monoalkylated benzene and dialkylated benzene; passing the second process stream into an intermediate point of a third fractionation means, which is operated at fractionation conditions which include a subatmospheric pressure, withdrawing a sidecut stream comprising monoalkylated benzene from the third fractionation means and dividing the sidecut stream into at least a first portion which is withdrawn as a product stream and a second portion which is passed into the upper half of a fourth fractionation means as reflux, and withdrawing a first net bottoms stream comprising the monoalkylated benzene and the dialkylated benzene from the third fractionation means; passing the first net bottoms stream into the fourth fractionation means, which is operated at fractionation conditions which include a subatmospheric pressure, withdrawing a second net bottoms stream comprising dialkylated benzene from the fourth fractionation means and withdrawing an overhead vapor stream comprising monoalkylated benzene from the fourth fractionation means; and passing the overhead vapor stream into the upper half of the third fractionation means.

The product linear alkylbenzene obtained in this manner may be used as the raw material or feedstock for the preparation of a true detergent or surface active agent. Excellent detergents may be produced from the alkylbenzene by first performing a sulfonation to produce a sulfonic acid derivative by contact with an agent such as sulfur trioxide. This derivative is then neutralized by passage into a saponification zone. The neutralization comprises the admixture of the sulfonation reactor effluent with an aqueous stream containing ammonia, sodium hydroxide or potassium hydroxide. The alkaline compound neutralizes the sulfonic acid to produce sulfonates such as water-soluble sodium alkylaromatic monosulfonate salts. Further information on sulfonation and saponification are available from many standard references and from U.S. Pat. Nos. 4,036,875 and 4,240,978. The product alkylate can also be subjected to other chemical reactions to produce other types of detergents. For instance, the alkylate may be nitrated to form a substituted mono-nitro derivative which is then catalytically reduced to a monoamino-substituted analog such as an alkylaniline or alkyltoluidine. The amine is then condensed with ethylene oxide or propylene oxide to introduce a hydrophilic polyoxyalkylene group on the amino nitrogen atom. This preferably forms a polyoxyalkylated detergent product having from about 10 to 30 oxyalkylene units per molecule. The condensation may be catalyzed by the presence of an alkaline catalyst such as sodium hydroxide.

The normal paraffin stream which is preferably produced in the fractionation zone is preferably passed into a catalytic paraffin dehydrogenation zone. In this zone the paraffins in admixture with hydrogen are contacted with a catalyst at an elevated temperature to produce additional feed olefinic hydrocarbons. A preferred set of dehydrogenation conditions includes a temperature of about 420° to about 545° C., a pressure from about 0.7 to about 13 atmospheres (preferably about 2 atmospheres) and a liquid hourly space velocity in the range of about 10 to 36. A catalyst comprising platinum, tin and chlorine supported on alumina spheres is preferred although other catalysts can be substituted. The recycled paraffins together with any feed paraffins charged to the overall process are heated to reaction conditions and preferably passed through a single catalyst bed. The effluent of the catalyst bed is partially condensed to allow a simple separation of a hydrogen-rich gas, a portion of which is withdrawn with the remainder being recycled to the reactor. The net condensate is passed into a stripping column wherein all hydrocarbons having fewer carbon atoms per molecule than the desired feed normal olefin(s) are removed overhead as a light ends stream. Further details on suitable dehydrogenation methods may be obtained by reference to U.S. Pat. Nos. 3,391,218; 3,448,165; 3,745,112 and 3,907,921. The catalyst and the configuration of the dehydrogenation reaction zone may be chosen as desired from any commercially feasible type of catalyst and reactor.

I claim as my invention:

1. A process for the production of alkylaromatic hydrocarbons which comprises the steps of:
   (a) contacting a first feed stream comprising a $C_7$-plus olefinic hydrocarbon with a second feed stream comprising an alkylatable aromatic hydrocarbon and with an alkylation catalyst in an alkylation zone operated at alkylation-promoting conditions and thereby producing an alkylation zone effluent stream which comprises a mixture of monoalkylated aromatic hydrocarbons, dialkylated aromatic hydrocarbons and high boiling point alkylation reaction by-products; and, (b) recovering a product stream of high purity monoalkylated aromatic hydrocarbon by fractionating the alkylation zone effluent stream in a fractionation zone in which:
  (i) a first process stream which comprises the monoalkylated aromatic hydrocarbon, dialkylated aromatic hydrocarbons, and other high boiling point reaction by-products is passed into a first intermediate point of a first fractionation column operated at a subatmospheric pressure;
  (ii) a first net bottoms stream comprising the high boiling reaction by-products, dialkylated aromatic hydrocarbons and the monoalkylated aromatic hydrocarbon is removed from the first fractionation column and passed into a second fractionation column operated at a subatmospheric pressure;
  (iii) a sidecut stream comprising the monoalkylated aromatic hydrocarbon is withdrawn from the first fractionation column at a higher second intermediate point;
  (iv) the sidecut stream is divided into at least a first portion which is withdrawn as the product stream of the process and a second portion which is passed into the second fractionation column at a point above the location at which the first net bottoms stream enters the second fractionation column;
  (v) an overhead vapor stream comprising the monoalkylated aromatic hydrocarbon is removed from the second fractionation column and passed into the first fractionation column at a point above said first intermediate point; and,
  (vi) a second net bottoms stream comprising the dialkylated aromatic hydrocarbon is withdrawn from the second fractionation column and removed from the process.

2. The process of claim 1 further characterized in that the alkylatable aromatic hydrocarbon of the second feed stream is benzene.

3. The process of claim 2 further characterized in that the alkylation catalyst comprises HF.

4. The process of claim 3 further characterized in that the sidecut stream is also divided into a third portion which is passed into the first fractionation column at a third point located above said second intermediate point.

5. The process of claim 4 further characterized in that the $C_7$-plus olefinic hydrocarbon of the first feed stream is a $C_{10}$-plus normal olefinic hydrocarbon.

6. The process of claim 5 further characterized in that the second net bottoms stream also comprises the high boiling alkylation reaction by-products other than dialkylated aromatic hydrocarbons which are present in the alkylation zone effluent stream.

7. The process of claim 3 further characterized in that a process stream which is rich in normal paraffinic hydrocarbons having the same number of carbon atoms per molecule as the $C_7$-plus olefinic hydrocarbon is also produced in the fractionation zone, and in that the process stream is passed into a dehydrogenation zone wherein $C_7$-plus olefinic hydrocarbons consumed within the alkylation zone are produced.

8. A process for the production of alkylaromatic hydrocarbons which comprises the steps of:
  (a) contacting a first feed stream which comprises both a $C_8$-plus normal olefinic hydrocarbon and a corresponding paraffinic hydrocarbon with a second feed stream which comprises benzene and with liquid phase HF in an alkylation zone operated at alkylation-promoting conditions and producing a hydrocarbonaceous alkylation zone effluent stream which comprises the paraffinic hydrocarbon, benzene, monoalkylated benzene and dialkylated benzene;
  (b) separating benzene from the alkylation zone effluent stream in a first fractionation means, and thereby producing a first process stream, which comprises the paraffinic hydrocarbon, monoalkylated benzene and dialkylated benzene;
  (c) separating paraffinic hydrocarbons from the first process stream in a second fractionation means, and thereby producing a second process stream, which comprises monoalkylated benzene and dialkylated benzene;
  (d) passing the second process stream into an intermediate point of a third fractionation means, which is operated at fractionation conditions which include a subatmospheric pressure, withdrawing a sidecut stream comprising monoalkylated benzene from the third fractionation means and dividing the sidecut stream into at least a first portion which is withdrawn as a product stream and a second portion which is passed into the upper half of a fourth fractionation means as reflux, and withdrawing a first net bottoms stream comprising the monoalkylated benzene and the dialkylated benzene from the third fractionation means;
  (e) passing the first net bottoms stream into the fourth fractionation means, which is operated at fractionation conditions which include a subatmospheric pressure, withdrawing a second net bottoms stream comprising dialkylated benzene from the fourth fractionation means and withdrawing an overhead vapor stream comprising monoalkylated benzene from the fourth fractionation means; and,
  (f) passing the overhead vapor stream into the upper half of the third fractionation means.

9. The process of claim 8 further characterized in that the overhead vapor stream enters the third fractionation means at a point above the elevation at which the second process stream enters the third fractionation means.

10. The process of claim 9 further characterized in that the overhead vapor stream enters the third fractionation means at an elevation above the point at which the sidecut stream is withdrawn from the third fractionation means.

11. The process of claim 10 further characterized in that a third portion of the sidecut stream is passed into the third fractionation means at an elevation above the point at which the sidecut stream is withdrawn from the third fractionation means.

* * * * *